United States Patent [19]

Halbritter

[11] 4,211,875

[45] Jul. 8, 1980

[54] PREPARATION OF 4-METHYL-5-CHLOROMETHYL-IMIDAZOLE

[75] Inventor: Klaus Halbritter, Mannheim, Fed. Rep. of Germany

[73] Assignee: BASF Aktiengesellschaft, Fed. Rep. of Germany

[21] Appl. No.: 974,248

[22] Filed: Dec. 29, 1978

[30] Foreign Application Priority Data

Jan. 3, 1978 [DE] Fed. Rep. of Germany ....... 2800148

[51] Int. Cl.$^2$ ............................................ C07D 233/64
[52] U.S. Cl. .................................................... 548/342
[58] Field of Search ......................................... 548/342

[56] References Cited

U.S. PATENT DOCUMENTS 4,104,473  8/1978  Sawa et al. ........................... 548/342

OTHER PUBLICATIONS

Grindley et al. J. Chem. Soc., 1927, pp. 3128–3136.
Hofmann Imidazole and Its Derivatives Part I pp. 99–100 N.Y., Interscience, 1953.
Noller Chemistry of Organic Compounds 2nd ed. p. 102 Philadelphia, Saunders, 1958.
Windaus Berichte (Deutsche Chem. Gesellschaft) 1909, vol. 42, pp. 758–763.

Primary Examiner—Natalie Trousof
Attorney, Agent, or Firm—Keil & Witherspoon

[57] ABSTRACT

4-Methyl-5-chloromethyl-imidazole is prepared in the form of its hydrochloride by direct chloromethylation of 4-methyl-imidazole, thus becoming readily available industrially as an intermediate.

3 Claims, No Drawings

PREPARATION OF 4-METHYL-5-CHLOROMETHYL-IMIDAZOLE

The present invention relates to a process for the preparation of 4-methyl-5-chloromethyl-imidazole, in the form of its hydrochloride, by chloromethylation of 4-methylimidazole.

4-Methyl-5-chloromethyl-imidazole hydrochloride has hitherto been prepared from 4-methyl-5-hydroxymethylimidazole by reaction with inorganic acid halides, as described by A. J. Ewins in J. Chem. Soc. 99 (1911), 2052–2059 or G. J. Durant et al. in J. Med. Chem. 19 (1976), 923–928. It is a disadvantage of these processes that 4-methyl-5-hydroxymethyl-imidazole must be used as a starting material, since this compound can only be prepared by relatively difficult and involved methods. For example, 4-methyl-5-hydroxymethyl-imidazole has hitherto been prepared from 4-methyl-imidazole-5-carboxylic acid esters by reduction with an alkali metal or with calcium, in liquid ammonia. This process is lengthy, expensive, and relatively difficult to carry out on an industrial scale because of the quantities of alkali metal in liquid ammonia which have to be handled; the process is described in German Laid-Open Application DOS No. 2,637,670.

I have found that 4-methyl-5-chloromethyl-imidazole hydrochloride can be prepared simply, even on an industrial scale, by reacting 4-methylimidazole, in aqueous solution, with formaldehyde or a formaldehyde oligomer, in the presence of an excess of hydrogen chloride, at from 25° to 160° C.

The following equation illustrates the invention:

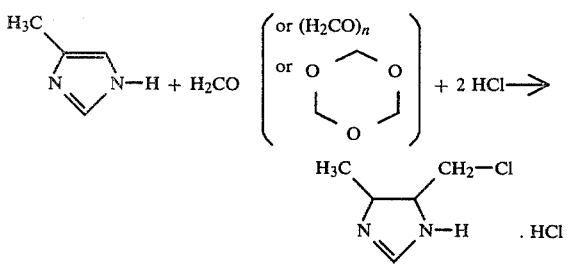

In the process according to the invention, the 4-methylimidazole is advantageously dissolved in aqueous concentrated hydrochloric acid; as a rule the solutions prepared are of 10–25% strength by weight.

The formaldehyde can be used as a conventional aqueous solution, containing 15–40% by weight of formaldehyde, as a gas or as one of its solid oligomers, eg. paraformaldehyde or 1,3,5-trioxane. The molar ratio of 4-methylimidazole to formaldehyde is advantageously from 1:1 to 1:1.5, these ratios relating to the monomer, even if formaldehyde oligomers are used.

The hydrogen chloride is used in excess, advantageously in the form of aqueous concentrated hydrochloric acid containing from 20 to 40% by weight of hydrogen chloride, or in the form of hydrogen chloride gas. Preferably, the reaction is carried out in a system containing both aqueous concentrated hydrochloric acid and hydrogen chloride gas. Hence, if the chloromethylation reaction is carried out under atmospheric pressure, it is advantageous to pass HCl gas through the reaction mixture, whilst if the reaction is carried out under pressure in a closed system, for example in an autoclave or a kettle, HCl gas can be additionally introduced, up to a pressure of 10 atmospheres.

The chloromethylation reaction according to the invention is carried out at from 25° to 160° C., preferably from 50° to 110° C. When working with a closed system, the pressure set up is the autogenous pressure corresponding to the particular temperature used.

The reaction is as a rule complete within a period of from 5 to 20 hours, depending on the temperature used. The progress of the reaction can be followed spectroscopically, for example by NMR spectroscopy; in the latter case, samples are taken from the reaction mixture and evaporated in the presence of concentrated DCl (in $D_2O$), after which the residue is analyzed.

The reaction product is worked up in the conventional manner, for example, by distilling off the solvent and recrystallizing the residue, for example from a lower alcohol, eg. ethanol. To achieve a better yield, it is advantageous to use a solvent containing hydrogen chloride.

The starting compound, ie. 4-methylimidazole, can be used in the pure form or as a technical-grade product.

It is surprising that the process according to the invention, ie. direct chloromethylation of an imidazole in the 5-position, should proceed by means of a smooth reaction which can be carried out on an industrial scale without interfering side-reactions. Such a simple chloromethylation reaction was unexpected since it is known that in reactions in a strongly acid medium imidazole is deactivated by protonization. The high selectivity with which the chloromethyl group is introduced into the 5-position, without interfering substitution in the 1- or 2-position, was also unexpected since, for example, the nitrogen atom in the 1-position carries a hydrogen which normally is easily replaceable. It is a further advantage that no interfering side-reactions of the resulting 5-chloromethyl compound, for example linking of imidazole rings via $CH_2$ groups, eg. the formation of diimidazolylmethane or of more highly condensed products, are observed.

The invention for the first time makes 4-methyl-5-chloromethylimidazole, an important intermediate for further imidazole derivatives, easily obtainable industrially.

4-Methyl-5-chloromethyl-imidazole makes it possible to obtain 4-methyl-5-hydroxymethyl-imidazole, or corresponding 5-alkoxymethyl derivatives, by advantageous methods, and these compounds can be used as intermediates, for example for the preparation of the drug cimetidine (N-cyano-N'-methyl-N''-[2-((4-methyl-5-imidazolyl)-methylmercapto)ethyl]-guanidine), as described in German Laid-Open Applications DOS Nos. 2,344,779 and 2,649,059.

4-Methyl-5-chloromethylimidazole can also itself be used as an intermediate for the preparation of cimetidine, by reacting the compound with cysteamine hydrochloride in boiling concentrated hydrochloric acid, or reacting it directly with cysteamine hydrochloride in the absence of a solvent.

It is interesting that direct chloromethylation reactions of imidazoles have not previously been disclosed. Furthermore, for example, the related compound 3,5-dimethyl-pyrazole, having one free NH group, cannot be caused to undergo a reaction which in the main results in chloromethylation at the carbon in the 4-position, since at room temperature the predominant reaction is substitution at the nitrogen whilst at elevated temperatures polymerization reactions occur, as described by J. Dvoretzky and J. Richter in J. Org. Chem. 15 (1950), 1285-1288.

The 4-methyl-5-chloromethylimidazole prepared according to the invention can easily be converted to the corresponding 5-alkoxy compounds, whilst according to the prior art, for example, the preparation of 4-methyl-5-alkoxymethyl-imidazoles is a complicated procedure starting from β-acetyl-vinyl-phosphonium halide, which is cyclized to 4-methyl-5-methyl-triphenylphosphonium-imidazole halide, the latter then being reacted with an alcohol/alcoholate mixture, as shown in the equation below (cf. German Laid-Open Application DOS No. 2,649,059):

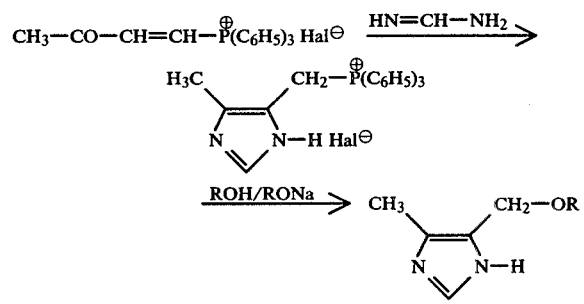

According to K. Wegner and W. Schunack, Arch. Pharm. 310 (1977), 380-385, 4-methyl-5-methoxymethylimidazole may be prepared by methoxymercuration of methyl vinyl ketone, which is a very toxic compound.

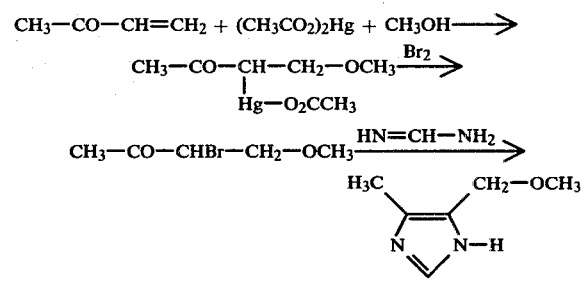

This process is unsuitable for industrial operation, especially because of the formation of mercury salts and because it entails working in liquid ammonia.

The Examples which follow illustrate the process according to the invention without implying any limitations.

EXAMPLE 1

218 parts of 37% strength formaldehyde solution are added dropwise, in the course of 4 hours, to a solution, at 80° C., of 167 parts of technical-grade 92.6% pure 4-methylimidazole in 826 parts of aqueous concentrated hydrochloric acid of about 36% strength by weight; at the same time a stream of HCl gas is passed into the mixture at the rate of about 65 parts by weight per hour, corresponding to 40,000 parts by volume per hour. The mixture is then heated for 20 hours at 80° C., whilst continuing to introduce HCl gas. After completion of the reaction, the aqueous hydrochloric acid is substantially distilled off under reduced pressure from a waterpump. 700 parts of a solution of HCl gas in ethanol ($\rho=0.88$) are added to the residue and the mixture is heated to the boil. It is then cooled to about +5° C. and the precipitate formed is filtered off, washed with a solution of HCl gas in ether, and dried under reduced pressure. 197.5 parts of 4-methyl-5-chloromethylimidazole hydrochloride of melting point 213° C. are obtained. A further 17.4 parts, of melting point 206° C., are obtained from the mother liquor and the ether wash solution, so that the total yield is 68.2%.

EXAMPLE 2

A mixture of 124 parts of aqueous concentrated hydrochloric acid of about 36% strength by weight, 25 parts of 92.6% pure 4-methylimidazole and 10.8 parts of paraformaldehyde is heated for 16 hours at 90° C. in a closed glass-linked kettle. The hydrochloric acid is then substantially distilled off under reduced pressure from a waterpump and the residue is dissolved in 160 parts of a boiling solution of HCl gas in ethanol ($\rho=0.88$). After the mixture has cooled, the crystals which have precipitated are filtered off, washed with a solution of HCl gas in ethanol and a solution of HCl gas in ether, and dried under reduced pressure. 20 parts of product, of melting point 214°-216° C., are obtained. A further 4.2 parts, of melting point 209°-210° C., are obtained from the mother liquor and the wash solutions, so that the total yield is 51.3%.

EXAMPLES OF FURTHER CONVERSIONS OF 4-METHYL-5-CHLOROMETHYL-IMIDAZOLE

I. 4-Methyl-5-ethoxymethyl-imidazole hydrochloride 2.0 parts of 4-methyl-5-chloromethyl-imidazole hydrochloride in 6.5 parts of absolute ethanol are boiled for 20 hours. The mixture is then evaporated almost to dryness and the resulting solid crystalline product is filtered dry on a fritted glass disk.

1.9 parts (90%) of 4-methyl-5-ethoxymethyl-imidazole hydrochloride of melting point 141°-143° C. are obtained. A further recrystallization from acetonitrile, to prepare analytically pure material, gives 1.6 parts (75%) of melting point 143° C.

| Analysis: | C | H | Cl | N | O |
|---|---|---|---|---|---|
| calculated: | 47.6 | 7.4 | 20.1 | 15.9 | 9.1 |
| found: | 47.3 | 7.2 | 20.7 | 16.1 | 9.1 |

II. 4-Methyl-5-hydroxymethyl-imidazole hydrochloride 67 parts of 4-methyl-5-chloromethyl-imidazole hydrochloride are dissolved in 200 parts of water and the mixture is stirred for 4.5 hours at 50°-60° C. The water is then substantially distilled off under reduced pressure from a waterpump and the crystal slurry is recrystallized from ethanol, the solution being cooled in ice. 43.4 parts (73%) of 4-methyl-5-hydroxymethyl-imidazole hydrochloride of melting point 238°-240° C. are obtained (the melting point given in the literature is 240°-242° C., cf. A. J. Ewins, J. Chem. Soc. 99 (1911), 2052.

A further 6.7 parts (11%) of product, of melting point 236°-239°, can be isolated by working up the mother liquor.

III. 4-Methyl-5-[(2-amino-ethyl)thiomethyl]-imidazole dihydrochloride (a) A solution of 50.1 parts of 4-methyl-5-chloromethylimidazole hydrochloride and 34.1 parts of cysteamine hydrochloride in 410 parts of aqueous 36% strength hydrochloric acid is boiled for 20 hours. The aqueous hydrochloric acid is then substantially distilled off under reduced pressure from a waterpump, and the pasty residue is dissolved in 80 parts of boiling ethanol. After cooling to room temperature, filtering off the product and drying it, 56.5 parts (78%) of the dihydrochloride, of melting point 193°–196° C., are obtained. A further 7.8 parts (11%) can be isolated by concentrating the filtrate; melting point 191°–194° C.

(b) 84 parts of 4-methyl-5-chloromethyl-imidazole hydrochloride, in the form of a fine powder, and 57 parts of cysteamine hydrochloride, also in the form of a fine powder, are mixed intimately and the mixture is heated in a solidstate reactor for 2 hours at 80° and then for 7 hours at 100°; the progress of the reaction can be followed by NMR spectroscopy or from the evolution of hydrogen chloride. 120 parts (98%) of 4-methyl-5-[(2-amino-ethyl)-thiomethyl]-imidazole dihydrochloride are obtained; the substance melts at 186°–189° C., after first sintering at about 181° C. A single recrystallization of the product from ethanol raises the melting point to 193°–195° C.

I claim:

1. A process for the preparation of 4-methyl-5-chloromethylimidazole hydrochloride, wherein 4-methylimidazole, in aqueous solution, is reacted with formaldehyde or a formaldehyde oligomer in the presence of an excess of hydrogen chloride, at from 25° to 160° C.

2. The process of claim 1, wherein the reaction is carried out in aqueous hydrochloric acid, while at the same time passing gaseous hydrogen chloride through the mixture, and using a molar ratio of 4-methylimidazole to formaldehyde of from 1:1 to 1:1.5.

3. A process as claimed in claim 1, wherein the reaction is carried out in a closed system under pressure.

* * * * *